United States Patent
Lam et al.

(10) Patent No.: US 12,042,643 B2
(45) Date of Patent: Jul. 23, 2024

(54) DRUG DELIVERY DEVICE, METHOD FOR MANUFACTURING A DRUG DELIVERY DEVICE AND USE OF A WELDED CONNECTION

(71) Applicant: Sanofi, Paris (FR)

(72) Inventors: Ngoc Jane Lam, Frankfurt am Main (DE); Tobias Stever, Frankfurt am Main (DE)

(73) Assignee: Sanofi, Paris (FR)

( * ) Notice: Subject to any disclaimer, the term of this patent is extended or adjusted under 35 U.S.C. 154(b) by 708 days.

(21) Appl. No.: 17/252,453

(22) PCT Filed: Jun. 24, 2019

(86) PCT No.: PCT/EP2019/066656
§ 371 (c)(1),
(2) Date: Dec. 15, 2020

(87) PCT Pub. No.: WO2019/243632
PCT Pub. Date: Dec. 26, 2019

(65) Prior Publication Data
US 2021/0252230 A1   Aug. 19, 2021

(30) Foreign Application Priority Data

Jun. 22, 2018 (EP) ..................... 18305796

(51) Int. Cl.
*A61M 5/32* (2006.01)
*A61M 5/20* (2006.01)
(Continued)

(52) U.S. Cl.
CPC ........ *A61M 5/3202* (2013.01); *A61M 5/2033* (2013.01); *A61M 5/24* (2013.01); *A61M 5/5086* (2013.01); *A61M 2207/00* (2013.01)

(58) Field of Classification Search
CPC .... A61M 5/3202; A61M 5/2033; A61M 5/24; A61M 5/5086; A61M 5/50; A61M 2207/00; A61M 5/20; A61M 2005/2006
See application file for complete search history.

(56) References Cited

U.S. PATENT DOCUMENTS 5,226,894 A * 7/1993 Haber ................. A61M 5/3243
604/240
5,733,244 A * 3/1998 Yasui ................. A61M 13/003
600/129
(Continued)

FOREIGN PATENT DOCUMENTS

CN 101489362 A 7/2009
CN 102316918 1/2012
(Continued)

OTHER PUBLICATIONS

PCT International Preliminary Report on Patentability in International Application No. PCT/EP2019/066656, dated Dec. 22, 2020, 9 pages.
(Continued)

*Primary Examiner* — Robert J Utama
*Assistant Examiner* — Neeraja Gollamudi
(74) *Attorney, Agent, or Firm* — Fish & Richardson P.C.

(57) ABSTRACT

A drug delivery device is proposed which comprises: a housing defining an interior; a reservoir which is adapted to contain a drug or contains a drug, the reservoir being retained in the interior; and a closure part which is secured relative to the housing and has to be disconnected from the housing to get access to the reservoir within the interior, wherein the closure part is secured relative to the housing by a connection, wherein the connection comprises a welded connection, and wherein the welded connection is formed between two join partners, i.e. a first join partner and a
(Continued)

second join partner. Further, a method for manufacturing a drug delivery device is disclosed as is a use associated with drug delivery devices.

20 Claims, 6 Drawing Sheets

(51) Int. Cl.
  *A61M 5/24* (2006.01)
  *A61M 5/50* (2006.01)

(56) References Cited

U.S. PATENT DOCUMENTS

| | | |
|---|---|---|
| 2002/0125297 A1 | 9/2002 | Stol et al. |
| 2005/0161442 A1 | 7/2005 | Bradley |
| 2008/0229570 A1 | 9/2008 | Koppitz et al. |
| 2009/0181194 A1 | 7/2009 | Zhang et al. |
| 2014/0036353 A1 | 2/2014 | Korogdahl |
| 2014/0054295 A1* | 2/2014 | Holtwick ............ B65D 11/20 220/502 |
| 2014/0316341 A1 | 10/2014 | Holtwick et al. |
| 2014/0364811 A1 | 12/2014 | Holtwick et al. |
| 2015/0112277 A1* | 4/2015 | Groeschke ............ A61M 5/24 604/93.01 |
| 2015/0144602 A1 | 5/2015 | Draht et al. |
| 2015/0280767 A1 | 10/2015 | Ames et al. |
| 2016/0001015 A1 | 1/2016 | Kücük et al. |
| 2016/0341234 A1 | 11/2016 | Germann et al. |
| 2017/0128676 A1 | 5/2017 | Spallek et al. |
| 2018/0050156 A1 | 2/2018 | Travanty |
| 2018/0304018 A1* | 10/2018 | Blondino ............ A61M 5/28 |

FOREIGN PATENT DOCUMENTS

| | | |
|---|---|---|
| CN | 102448706 | 5/2012 |
| CN | 103764203 A | 4/2014 |
| CN | 103945882 A | 7/2014 |
| CN | 103957965 A | 7/2014 |
| CN | 104507520 A | 4/2015 |
| CN | 104540628 | 4/2015 |
| CN | 104619476 | 5/2015 |
| CN | 104647741 A | 5/2015 |
| CN | 105828851 | 8/2016 |
| CN | 106102985 A | 11/2016 |
| CN | 106233002 A | 12/2016 |
| CN | 106456893 | 2/2017 |
| CN | 115091768 A | 9/2022 |
| JP | 2015-524327 | 8/2015 |
| JP | 2015-529121 | 10/2015 |
| SG | 170391 | 6/2011 |
| WO | WO 1996/027533 | 9/1996 |
| WO | WO 2010/043533 | 4/2010 |
| WO | WO 2010/094916 | 8/2010 |
| WO | WO 2010/112562 | 10/2010 |
| WO | WO 2012/123565 | 9/2012 |
| WO | WO 2012/146680 | 11/2012 |
| WO | WO 2014/023771 | 2/2014 |
| WO | WO 2014/044741 | 3/2014 |
| WO | WO 2015/078758 | 6/2015 |
| WO | WO 2018/024624 | 2/2018 |

OTHER PUBLICATIONS

PCT International Search Report and Written Opinion in International Application No. PCT/EP2019/066656, dated Aug. 6, 2019, 12 pages.

* cited by examiner

DRUG DELIVERY DEVICE, METHOD FOR MANUFACTURING A DRUG DELIVERY DEVICE AND USE OF A WELDED CONNECTION

CROSS REFERENCE TO RELATED APPLICATIONS

The present application is the national stage entry of International Patent Application No. PCT/EP2019/066656, filed on Jun. 24, 2019, and claims priority to Application No. EP 18305796.7, filed on Jun. 22, 2018, the disclosures of which are incorporated herein by reference.

TECHNICAL FIELD

The present disclosure relates to a drug delivery device, a method for manufacturing a drug delivery device and a use.

BACKGROUND

Drug delivery devices, especially but not exclusively disposable ones, which are disposed of after one use-cycle, i.e. when the amount of drug which the device is designed to dispense has been dispensed from the device, either as a single dose or distributed over a plurality of doses, are usually provided by the manufacturer in a pre-assembled form. That is to say, a reservoir with the drug and optionally a drive mechanism, which is designed to drive delivery of the drug from the reservoir are assembled to form the device. It is usually not intended that the drug delivery device should be disassembled again. Nevertheless, this may be possible, particularly for technically competent people with the goal to disassemble the device. In recent times, it has been observed that drug delivery devices are disassembled by non-authorized persons and the reservoirs are manipulated, e.g. to substitute an emptied reservoir with a full one or to remove drug from the reservoir and to replace the removed drug with a different substance, not even necessarily a drug. Thereafter, the device can be assembled again and sold under the label of the original manufacturer, e.g. on the black market, although it does not contain the drug which it should contain, e.g. the one which is shown on the label. Such criminal activities can be very profitable especially for high-priced drugs or drugs, which are widely and/or often used, such as insulin, for example. Of course, if the user uses a device which has been tampered with or manipulated, e.g. in the way as has been described above, this might have fatal, potentially even lethal, consequences for the user.

SUMMARY

It is an object of the present disclosure to provide improvements in association with drug delivery devices. This object is achieved by the subject-matter defined in the independent claims, for example. Advantageous embodiments and refinements are disclosed herein below and are also subject of the dependent claims.

One aspect of the present disclosure relates to a drug delivery device. Another aspect relates to a method of manufacturing a drug delivery device. Yet another aspect relates to a use associated with a drug delivery device. It should be readily appreciated that features, which are disclosed below in conjunction with one of these aspects can be applied for the other aspects as well. For example, features disclosed in conjunction with the device can also be applied for the method or the use and vice versa. Moreover, features disclosed in conjunction with different embodiments can also be applied in combination with the features of any other disclosed embodiment. Also, features disclosed in combination with one another should be regarded as being disclosed on their own without requiring the other features of the combination.

In an embodiment, the drug delivery device comprises a housing. The housing may define an interior, e.g. of the drug delivery device. The housing may be tubular, for example. The housing may be an elongate housing. The housing may define the exterior contour of at least a section of the drug delivery device, e.g. of a majority of the drug delivery device as seen along an axial direction, e.g. from the proximal end of the device to its distal end.

In an embodiment the drug delivery device further comprises a reservoir. The reservoir expediently is adapted to contain a drug or contains a drug. The reservoir may be pre-filled. The reservoir may be retained in the interior of the housing. A length of the housing, e.g. the axial extension from the proximal end to the distal end of the housing, may be great enough to accommodate the entire reservoir within the housing. The drug delivery device may be a disposable drug delivery device.

In an embodiment, the drug delivery device further comprises a closure part. The closure part may be secured relative to or connected to the housing. The closure part may have to be disconnected from the housing to get access to the reservoir within the interior, for example to remove the reservoir from the housing or to manipulate the content of the reservoir. The closure part may have to be removed such that the reservoir can be tampered with, for example to substitute the drug within the reservoir can be substituted by another drug or substance or such to remove the entire reservoir.

In an embodiment, the closure part is secured relative to the housing by a connection. The connection may be or may comprise a tamper-evident connection. A tamper-evident connection may be a connection which can only be released in such a way that after it has been released once, it is perceivable for a person from the appearance of the parts which were forming the connection that the connection has been released once already. That is to say, from the appearance of the parts involved in the connection, it can be judged whether the device has been tampered with, i.e. whether the connection has been released. The connection may be designed as a permanent connection. A permanent connection can only be released by destroying or damaging one of the parts involved in the connection, e.g. so that the connection cannot be established once again, particularly not without additional measures. The connection may be or may comprise a welded connection, e.g. comprising or consisting of one weld or welded spot or more welds or welded spots. A welded connection is permanent and/or tamper-evident. By means of a permanent, tamper-evident, and/or welded connection, it can be achieved that the device cannot be disassembled without severe or permanent impact on the parts involved in the connection between the closure part and the housing. Thus, manipulation activities as discussed above are less likely to occur, are more easily detectable, and/or are made more difficult by employing such a connection. If the connection between the closure part and the housing is broken or released, it is immediately evident that the device has been tampered with. A welded connection is particularly advantageous for this purpose, as there are no additional parts required for the welded connection. The welded connection can be realized without having a connection material employed between two parts, which have to be joined to one another. Rather, it is a direct part-to-part bond or joint which can be effected by welding. The welded connection may be a laser-welded connection.

In an embodiment, the closure part is axially and rotationally locked relative to the housing, preferably by means of the connection. Thus, it can be achieved that the housing and the closure part form a protective entity for the interior of the housing and cannot be moved relative to one another. If they should be moved, the connection preferably has to be released.

In an embodiment, the connection has to be destroyed to disconnect the closure part from the housing. If the connection is destroyed, re-connecting the closure part and the housing may be impossible on account of the damage caused during the disconnection.

In an embodiment, the connection, particularly the welded connection, is formed or established between two join partners, i.e. a first join partner and a second join partner. The respective join partner may be a part of the drug delivery device. The respective join partner may be a plastic part. The welded connection may be formed by a plastic-to-plastic bond between the two join partners.

In an embodiment, at least one of the join partners has or both of the join partners have at least one molten and/or hardened area or joining area. The molten and/or hardened areas may form the welded connection, e.g. in a boundary area between the join partners, or may adjoin the welded connection. Outside of the molten and/or hardened areas, the join partners may not be connected. Both join partners may have a non-molten area. The respective non-molten area may surround the molten and/or hardened area. Thus, the welded connection may be a localized connection. In order to establish the welded connection, energy, i.e. electromagnetic radiation energy, may be applied to the at least one join partner or both join partners to melt the join partner. Once the respective melted material has hardened or solidified again, the molten and hardened area is formed.

In an embodiment, the welded connection is arranged closer to an exterior surface of the drug delivery device than the second join partner and/or closer to an exterior surface of the drug delivery device than a surface of the second join partner facing away from the welded connection. The exterior surface may be a side surface of the device. The exterior surface of the device may be formed and/or its shape may be defined by the first join partner or by an additional part of the device. The first join partner, in particular an outwardly facing surface thereof—e.g. a surface facing towards the exterior of the device—, may be arranged between the welded connection and the exterior or the exterior surface of the drug delivery device. The outwardly facing surface may form the exterior surface or may be an additional surface, which is arranged between the exterior surface and the welded connection. The exterior surface may define or comprise an irradiation area, where electromagnetic radiation, e.g. laser radiation is radiated onto this surface during the manufacturing process of the device. Thus, when energy is applied to the drug delivery device to generate the connection, the energy can be transferred through the first join partner until it reaches the second join partner, for example to melt the second join partner. Preferably, the two join partners have different absorption properties for the radiation which is used to generate the connection. The first join partner expediently absorbs less than the second join partner.

In an embodiment, the extension of the molten and/or hardened area in the second join partner away from the welded connection or from the first join partner is greater than the extension of the molten and/or hardened area of the first join partner away from the welded connection or from the second join partner. This configuration may result from the different absorption properties.

In an embodiment, the welded connection is inwardly offset from an exterior surface of the housing. The exterior surface of the housing may be that surface of the housing closest to the welded connection. In particular, the exterior surface may be that surface, through which energy is transferred from the exterior of the device to the interior of the housing in order to generate the connection.

If the first join partner is arranged closer to the exterior than the second join partner, the welded connection is not easily perceivable from the exterior. Thus, a person with the intention to manipulate the device may be unaware that the parts will be damaged severely or permanently if the device is disassembled when he attempts the manipulation on that particular type of device for the first time. The damages caused during the disassembling may hinder the person to try the manipulation again as he will recognize that the risk of permanently damaging components is high and the concept of tampering with device is not profitable anymore.

In an embodiment, the first join partner and the second join partner are configured to have different absorption coefficients for an electromagnetic radiation, e.g. laser radiation. The electromagnetic radiation is expediently the one, which is used to generate the connection. The absorption coefficient of the first join partner is preferably less than the one of the second join partner for the electromagnetic radiation. Accordingly, the electromagnetic radiation may travel through the first join partner from the exterior of the housing more easily and can be absorbed, at least predominantly, in the second join partner to melt the second join partner and generate the welded connection, preferably in an area of mechanical contact between the first and second join partners. From the second join partner energy, e.g. heat or thermal energy, may be transferred to the first join partner on account of the contact between the join partners. The transferred energy may cause the first join partner to melt in the area where the first join partner contacts the liquid molten material of the second join partner. On account of the indirect transfer of energy from the radiation source, the first join partner may be melted to a lesser extent than the second join partner.

In an embodiment, the first join partner and the second join partner have the same or similar melting temperatures, e.g. with a deviation of 20% or less or 10% or less. This facilitates the indirect melting of the first join partner via the heat transferred to it via the molten liquid material of the second join partner.

In an embodiment, the melting temperature of the first join partner is less than the one of the second join partner. In this case, if heat losses will occur after the second join partner has been melted locally, melting the first join partner via the heat transferred to it via the second join partner is facilitated.

In an embodiment, the second join partner comprises absorber particles configured to absorb electromagnetic radiation, in particular laser radiation. This radiation is expediently the one, which is used to generate the connection. Thus, the absorption of energy in the second join partner can be selectively increased over the one in the first join partner by providing the absorber particles. The absorber particles may be carbon black particles or infrared absorber particles. Carbon black particles have a black colour, i.e. they absorb in the visible spectral range, whereas infrared absorber particles usually have a colour, which is not black. Via the absorber particles or pigments it can be achieved that the energy of the electromagnetic radiation is predominantly absorbed in the second join partner.

In an embodiment, the first join partner is transparent for electromagnetic radiation. The electromagnetic radiation is in particular the one, which is used for the welded connection. In this context, "transparent" may mean that the first join partner absorbs the electromagnetic radiation to a lesser extent than the first join partner. Particularly, when the first join partner is irradiated with radiation of an energy or intensity, which is sufficient to melt the second join partner, this energy preferably is not sufficient to melt the first join partner.

In an embodiment, the electromagnetic radiation is radiation in the visible spectral region or in the ultraviolet or infrared spectral region.

In an embodiment, the first and the second join partners are brought into mechanical contact before the connection is generated. Thus, in the region outside of the welded connection, the two join partners may abut. The mechanical contact may strengthen the stability of the welded connection and also facilitates the transfer of thermal energy from the second join partner to the first join partner to melt the first join partner locally.

In an embodiment, at least one of the join partners is elastically deformable. Thus, before the connection is established, one of the join partner can be elastically deformed. The elastic restoring force which tends to establish the undeformed shape may increase the contact force acting between the first and the second join partner. The contact force maintains the surfaces which should be connected in mechanical contact. The stability of the connection may be increased by the increased contact force.

In an embodiment, at least one of the join partners comprises a join feature, e.g. an arm-like feature. The join feature may be elastically and/or resiliently connected to a body or main body of the join partner. The join feature may be pivotally connected to the main body. The join feature may be integrally formed with the main body. The respective join partner may be a unitary part. The join feature may be arranged between the body and the other join partner of the connection. The connection between the join partners is expediently established between the join feature and the other join partner. Preferably, the join feature is deflected resiliently before the connection is established. Thus, the resilient force may act on the contact area between the join partners and increase the contact force before the welding is conducted, which has the advantages discussed above.

In an embodiment, the closure part is one of the join partners. The closure part may be the second join partner.

In an embodiment, the housing is one of the join partners. The housing may be the first join partner.

In an embodiment, the first join partner may be different from the housing.

If the housing is one of the join partners, the housing is expediently transparent for the electromagnetic radiation. If the closure part is one of the join partners, the closure part is expediently configured to absorb the electromagnetic radiation.

In an embodiment, the closure part is one of the join partners and the other join partner is different from the housing. Thus, the housing does not have to be transparent for the radiation which increases the number of materials the housing can be manufactured from. The join partner which is different from the housing may be retained in a defined position relative to the housing by means of the welded connection.

In an embodiment, the closure part is secured relative to the housing in a force-fit-free and/or a form-fit-free manner. Thus, no force-fit and/or form-fit connection such as a snap-fit connection may be necessary to secure the closure part relative to the housing.

In an embodiment, the closure part is secured relative to the housing only by means of the welded connection. Thus, if the welded connection is destroyed, the closure part cannot be connected again to the housing without employing an expensive welding process again. This may not be trivial or even impossible, as the join partners may have been permanently deformed during the first welding process already. The resulting expenditure might hinder criminals to attempt tampering with drug delivery devices as the profits are reduced.

In an embodiment, one of the join partners comprises a connection feature. The connection feature may be adapted to establish a positive-fit connection or form-fit connection, e.g. a snap-fit connection, with the other join partner, preferably preventing disconnecting the two join partners without releasing the form-fit or positive-fit connection. The connection feature may be a snap feature. The welded connection may be provided between the connection feature and the other join partner. Thus, destroying the welded connection may also render the connection feature useless.

In an embodiment, both join partners are accessible from the exterior of the drug delivery device. Thus, both join partners are preferably manipulatable or touchable by a user of the drug delivery device.

In an embodiment, the housing is tubular and/or the closure part closes an end of the housing, such as the proximal end of the housing. The proximal end of the housing may have an opening which is shaped to receive the reservoir and/or the closure part. The closure part and the housing may be adjusted for a form-fit engagement or form-fit connection, e.g. a press-fit connection, with one another.

The end designated with "proximal end" may be that end of the housing or of a different part of the drug delivery device, which is arranged furthest away from the dispensing end of the drug delivery device. That end of the housing or the different part of the drug delivery device, which is arranged closest to the dispensing end, may be the "distal end" of the housing or the different part.

In an embodiment, the housing comprises an aperture. One of the join partners, e.g. the first join partner, may be arranged in the aperture. The join partner, which is arranged in the aperture, may be retained in the aperture by the welded connection to the other join partner. The housing may not be involved as a join partner in the welded connection in this case. Thus, if the welded connection is broken or released, the join partner may be removed from the aperture. This may indicate to the user that the device has been tampered with. The aperture may be shaped so as to widen as seen from the interior to the exterior. In other words, the aperture may taper, i.e. reduce in cross-section, e.g. as seen along the radial direction, from the exterior to the interior. The join partner which is arranged in the aperture may be shaped so as to conform to the aperture. A movement of the join partner within the aperture towards the interior may be prevented on account of the shape of the join partner which is adjusted to the one of the aperture. A movement of the join partner form the aperture towards the exterior away from the other join partner may be prevented by the other join partner which is arranged in the housing and configured so as to not be movable through the aperture, e.g. by appropriate size and/or shape, and the (welded) connection between the join partners. The aperture in the housing may be closed by the join partner. The aperture and the join partner may be adjusted to each other to prevent angular and/or axial movement of the join partner and the housing relative to one another.

In an embodiment, the housing comprises an opening, where the welded connection is viewable from the exterior of the housing through the opening and/or accessible through the opening.

In an embodiment, the connection between the join partners cannot be viewed and/or accessed from the exterior of the drug delivery device. This measure may avoid that the connection can be modified from the exterior before the device is attempted to be disassembled. Expediently, the housing covers the connection and, preferably, an area surrounding the connection. A side surface of the housing may cover the connection.

In an embodiment, the welded connection comprises a plurality of separate welds between the two join partners. That is to say, in a single connection area, a plurality of welds may be generated, such that the connection is strengthened in this area.

In an embodiment, the drug delivery device comprises a plurality of welded connections, which are distributed circumferentially over the drug delivery device at different connection areas.

In an embodiment, the drug delivery device comprises a drive mechanism. The drive mechanism may be configured to drive the dispensing of the drug from the reservoir, when the device is operated to dispense the drug from the reservoir.

In an embodiment, the drug delivery device comprises a spring, such as a drive spring. The spring may be part of the drive mechanism. The spring may provide the energy for the dispensing operation. The spring may be pre-biased to drive the dispensing of the drug from the reservoir. The bias may be reacted or reactable by the welded connection. The welded connection may be configured to react the spring force, e.g. when the device is operated to dispense drug and/or when it is stored. The welded connection(s) may be configured to react only a part of the spring force or the entire spring force.

In an embodiment, the welded connection is configured to react a drive force acting during the dispensing of the drug from the reservoir, where the drive force may be exerted by the drive spring.

In an embodiment, the drug delivery device is an auto-injector. Auto-injectors are often used for high-cost drugs, such that an anti-counterfeiting or tamper-evidence mechanism, which can be employed by the welded connection, is particularly advantageous for auto-injectors.

In an embodiment, the reservoir is a syringe or a syringe-type reservoir.

In an embodiment, the drug delivery device comprises a needle. The needle may be retained in the housing. The needle may be secured to the reservoir. The drug delivery device may have two states, a first state where the needle is shielded in the interior of the drug delivery device and a second state, where the needle can protrude from the drug delivery device. In the first state, the needle may not be visible for a user from the exterior. In the second state, the needle may penetrate the skin of the subject into which the drug should be dispensed. The needle may point to the distal end of the housing in the first state and/or protrude from the distal end in the second state. The needle may be retained in the housing when the device is not used. In auto-injectors usually the entire drug in the reservoir is dispensed in a single dispensing action by means of energy stored in an energy reservoir, such as a spring. Thus, in auto-injectors, the dispensing action has to be triggered, but a dose setting action, which sets the size of the dose may not be necessary. Auto-injectors are often used in emergency situations.

In an embodiment, the connection may be an anti-counterfeiting feature and/or a tamper indicator. Thus, if the (welded) connection has been damaged, it is indicated to the user, that the device is a counterfeited device or has been tempered with.

In an embodiment of the method of manufacturing a drug delivery device, a housing may be provided. Afterwards, a reservoir may be inserted into the housing. The reservoir may contain a drug. Thereafter, a closure part may be arranged relative to the housing and to the reservoir in a predetermined position. Thus, the closure part and the housing are are arranged in a desired or predetermined position after this step. Then, the closure part may be secured relative to the housing in the predetermined position by welding such as by laser welding or ultrasonic welding.

In an embodiment, securing the closure part by welding relative to the housing comprises the step of providing a laser. Thereafter, laser radiation may be generated by means of the laser.

An area of the exterior surface of a part, which is preferably transparent for the laser radiation, is irradiated with the laser radiation, such that the laser radiation propagates through the part, e.g. towards the interior of the housing. The part may be the housing or another part. The part may be one of the join partners described above, e.g. the first join partner. Thereafter, a weld may be generated at a position within the interior of the housing. This position is offset from the irradiated area of the exterior surface along the propagation direction of the laser radiation, e.g. towards the interior of the housing. The position may be arranged at the boundary of the part with another part, e.g. the other join partner.

In an embodiment of the use, a welded connection between two parts of the drug delivery device is used as a tamper indicator and/or an anti-counterfeiting feature.

Further features, advantages and embodiments of the present disclosure will become apparent from the following description of the exemplary embodiments in conjunction with the drawings.

DETAILED DESCRIPTION

Identical features, features of the same kind and identically acting features may be provided with the same reference numerals in the drawings.

Figure 1:
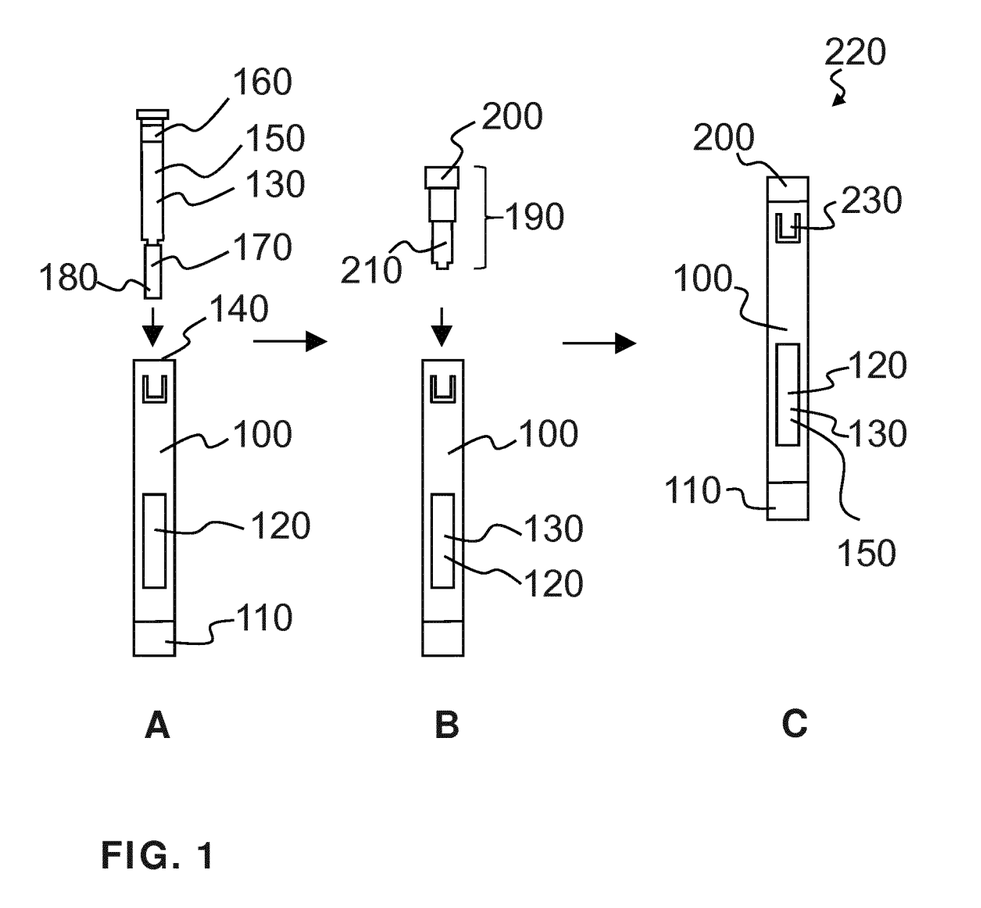
FIG. 1 schematically illustrates an assembling or manufacturing process of a drug delivery device on the basis of three representations A through C.

FIG. 1 illustrates an embodiment of a manufacturing process for a drug delivery device 220. In this embodiment, the drug delivery device is an auto-injector. It is however also possible to use different devices, especially disposable devices in the context of the present disclosure.

Basically, the assembling process or manufacturing process has three basic steps, which are illustrated in representations A to C. In the first step, which is shown in representation A, a housing 100 is provided. As is shown, the housing 100 is tubular and has an elongate shape. The housing 100 may be part of a housing unit, which, in addition to the housing, may comprise further elements for the drug delivery device 220, such as a cap 110, and also elements, which are moved during operation of the device, such as a trigger device or a needle shield, which may be realized by the same component. The trigger device may be covered by the cap in the depicted situation. If the cap is removed before dispensing a drug, the trigger device becomes accessible. If the trigger device is triggered during operation of the drug delivery device, e.g. by displacing it relative to the housing 100, the drug may be dispensed from the device. However, as the particular way of operation of the device is not the main concern of the present discussion, it is not explicitly shown in the drawings. The housing 100 further comprises a window 120. As is apparent from representation A, a reservoir 130, e.g. pre-filled, is inserted into the housing 100. For example, the reservoir 130 may be inserted into the housing via a proximal opening 140 of the housing 100. The reservoir 130 comprises a drug 150, e.g. a liquid drug, or medicament.

The term "drug", as used herein, preferably means and the term "medicament" means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [xMet(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The reservoir 130 may be a pre-filled syringe. The proximal end of the syringe may be closed by a moveable bung or a stopper 160 as depicted. At the distal end of the reservoir 130 a needle unit 170 may be arranged. The needle unit 170 may comprise a needle (not explicitly illustrated) and/or a needle cover 180. The needle cover 180 expediently covers the needle. The needle cover 180 may be coupled to the cap during the assembling process such that it is removed together with the cap 110 when the device 220 is prepared for operation. The reservoir may be moved relative to the housing, until an end position has been reached, e.g. defined by an end stop which is contacted by the reservoir or the needle unit.

After the reservoir 130 has been inserted into the housing 100, a further unit, such as a mechanism unit 190 is connected to the housing 100 as shown in representation B. The mechanism unit 190 may be guided into the interior of the housing 100 via the proximal opening 140 as depicted. The mechanism unit 190 comprises a closure part 200. Instead of being a mechanism unit with additional parts which may move during the dispensing action, the unit may just be a closure part with one or more than one components which are stationary during the dispensing process for dispensing drug from the device 220.

The mechanism unit 190 may, in addition to the closure part 200, comprise a bung driver 210. The bung driver 210 may be spring-biased. For this purpose, the device 220 may have a drive spring 213, but may be retained in the interior of the bung driver 210, for example. The bung driver 210, which may have a rod-like configuration, may be arranged to drive the bung 160 distally relative to the reservoir 130 in order to dispense drug from the device. After the closure part 200 has been guided into the housing to an end position, the closure part 220 is secured relative to the housing 100, preferably such that relative rotational and/or relative axial movement of the closure part or mechanism unit relative to the housing 100 is prevented.

The drug delivery device 220 which is manufactured or assembled is shown in representation C. The reservoir 130 and, in particular, the drug 150 in the reservoir is visible through the window 120 for the user. The window 120 permits a visual check, whether drug is contained in the device 220. The closure part 200 and the housing 100, and preferably also the remaining parts of the device, maybe except the drive spring or other springs, which may be of metal, are preferably plastic parts.

Figure 2:
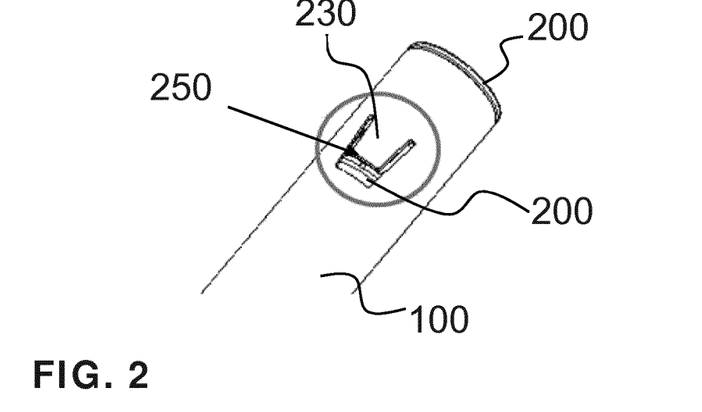
FIG. 2 shows a schematic view of a part of a drug delivery device.

The securing between the closure part and the housing may be effected by means of one or more connection features 230. The connection feature 230 may be a snap-fit feature or a clip feature. The connection feature 230 may engage a corresponding feature on the closure part 200 to secure housing and closure part to one another. Accordingly, closure part 200 and housing 100 may be connected to one another by a force-fit or a form-fit connection. The connection feature 230 may be arranged on the exterior of the housing, but may be covered with a label (not shown). The label may contain information about the content of the reservoir, such as drug-type or concentration and/or both. FIG. 2 shows a more detailed representation of the housing 100, the connection feature 230 and its connection to the closure part 200 of the drug delivery device, where the region with the connection feature 230 is highlighted by the circular line. As the connection feature 230 is accessible from the exterior of the drug delivery device—potentially after removing the label which is usual an easy task—, there are ways to disassemble the device, as a skilled person can release the connection between the connection feature 230 and the closure part 200, remove the closure part from the housing 100 and either replace an empty reservoir with a new one with a content chosen by the person and not by the manufacturer or tamper with the content of the reservoir, if the reservoir is still full. Thereafter, the device can be reassembled, and the user might use the device with a content, which he is not aware of, which may, of course, have fatal and potentially even lethal consequences for the user.

In the following concepts or embodiments are disclosed, which facilitate that drug delivery devices can be made more secure with respect to tampering and/or counterfeiting. All of the concepts do employ a welded connection or a plurality of welded connections by means of which the closure part 200 is secured relative to the housing 100. The welded connection is preferably a laser-welded connection. Thus, laser light can be radiated onto one or two plastic parts, such as housing and a closure part, and be absorbed in at least one of these parts, such that at least one of the parts melts locally and a stable connection to another part can be achieved after the molten material has hardened again. A laser-welded connection has the advantage that no additional securing material, such as an adhesive, has to be used and it also is very stable. Further, during a welding-process the join partners, which are involved in forming the welded connection, may be plastically deformed, such that, if a welded connection is destroyed, a welded connection with the same characteristics cannot be easily re-established under the same conditions and also with the same mechanical requirements, for example with respect to force reaction capabilities. Thus, if the connection has been destroyed once, it is difficult, to re-establish the connection with the same characteristics. The welded connection maybe employed in addition to the connection established by the connection feature or instead thereof. The welded connection may be the only connection between the closure part 200 and the housing 100 which prevents removal of the closure part from the housing. The welded connection or the plurality of connections may be stable enough to react the drive force exerted by the drive spring during operation of the device. It should be appreciated that features described in the following embodiments can be combined with one another.

Figure 3:
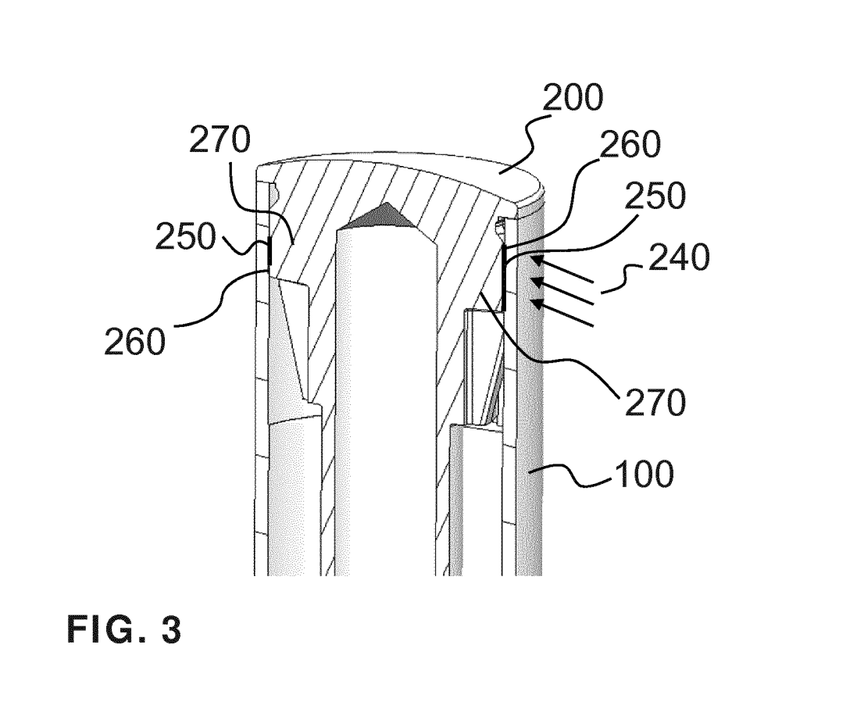
FIGS. 3 to 5 each illustrate one embodiment of a drug delivery device and a method of manufacturing the device, where the device has a welded connection, on the basis of a schematic sectional view.

FIG. 3 shows one embodiment, which utilizes laser welding in order to connect the closure part 200 with the housing 100. FIG. 3 illustrates a schematic sectional view in the region of the proximal end of the drug delivery device 220 depicted in FIG. 1 or 2. The closure part 200 has been inserted into the housing 100 already. A distally facing surface of the closure part 200 may abut a proximally facing surface of the housing 100. In the depicted embodiment, the welded connection is formed between the closure part 200 and the housing 100. The housing 100 is preferably made of a transparent material, i.e. transparent for the radiation which should be used for the laser welding process. The transparent material may be a thermoplastic material, e.g. a non-reinforced thermoplastic material. Such materials are usually transparent over a comparatively wide range of wavelengths. The closure part 200 may be provided with absorbers or absorbing particles, such as carbon black particles and/or infrared absorbers. The absorber particles are configured to absorb laser radiation. The laser radiation may be radiation within the visible spectral range, the infrared spectral range and/or the ultraviolet spectral range. For example, for the wavelength of the radiation which is used, the absorptivity in the closure part may be at least twice the absorptivity in the housing. The ratio of the absorptivity (usually specified in percent) of the closure part to the one of the housing may be greater than or equal to any arbitrary one of the following values: 2, 3, 4, 5, 6, 7, 8, 9, 10, 20, 30, 50, 100, 120, 150, 170, 200. A melting temperature of the housing 100 may be less than the one of the closure part, e.g. by 10% or less.

When the closure part 200 has been inserted into the housing 100, there is expediently a region, where the closure part mechanically contacts the housing. For example, a radially outwardly facing surface of the closure part 200 may contact a radially inwardly facing surface of the housing, preferably in a press-fitting configuration, where one of the parts may be elastically deformed, e.g. to increase the contact force at the designated welding position.

In the surface region with the mechanical contact the formation of a welded connection 250, in particular one of high stability, is facilitated. As the housing 100 is laser transparent, the laser radiation 240 may be radiated from the exterior of the housing 100 onto a position or an area, which axially overlaps with the area, where the closure part and the housing abut radially, i.e. where the welded connection should be formed. The laser radiation 240 travels through the housing 100, which expediently does not melt on account of its transparency, hits the closure part 200 and is absorbed therein. In consequence, the closure part 200 is heated until it melts locally. The material of the housing 100 in the region of the inner surface of the housing, which is contacted by closure part 200, may melt as well, for example on account of the heat transferred to it by the molten closure part material. The molten materials of the different parts may contact one another to form a stable material connection once they have hardened again, e.g. via a plastic-to-plastic bond. When the laser radiation 240 is removed or switched off, the molten material(s) can harden again and a reliable and stable connection between the closure part 200 and the housing is obtained.

The connection 250 is expediently stable enough to react the drive force occurring during the driving operation of the drug delivery device, e.g. exerted by a drive spring. Drive forces, which occur during the operation of auto-injectors may be greater than or equal to 5 N, greater than or equal to 10 N, greater than or equal to 15 N, or greater than or equal to 20 N, for example. A force may be less than or equal to 45 N, less than or equal to 40 N, less than or equal to 35 N or less than or equal to 30 N. For example, the maximum force occurring during a driving operation, e.g. the initial spring force, may be 26 N. Accordingly, the connection is expediently designed to be stable enough to react forces in these ranges. The welded connection or the plurality of welded connections may be configured to react at least a part of the force, e.g. 50 or more, 75% or more, 80% or more, 85% or more, 90% or more, or 95% or more. The welded connection may be configured to react, e.g. be stable when exposed to, forces in the ranges disclosed further above even if the force is not a drive force, but e.g. a bias spring force not used during a driving operation.

In FIG. 3, the welded connection 250 is shown. One or more radially facing surfaces 260 of the closure part 260, which face the inner surface of the housing 100, are in contact with the inner surface of the housing. The respective surface 260 may be formed by means of radially oriented protrusions 270, i.e. one or more protrusions, provided in the closure part 200. Of course, the housing could be provided with radially inwardly extending protrusions to provide the mechanical contact to the closure part. However, in this case, the moulding of the housing will be more complicated or expensive, such that the depicted arrangement is preferred, whereas the arrangement where the protrusions are provided in the housing is, of course, also possible.

The closure part 200 and the housing 100 are adjusted such that, in the mounted position, before the welded connection is created, the closure part and the housing are connected via press-fit connection. The outer diameter of the closure part 200 may be equal to the inner diameter of the housing in the respective region where mechanical contact should be made between housing and closure part 200. One of the diameters may be slightly over or under dimensioned such that, when the two parts art in the fitted configuration as depicted, at least on is slightly elastically deformed. The elastic restoring force may increase the pressure on the contact surface. The increased pressure may assist in providing a particularly stable welded connection. It has been observed, that even a small slit between the two parts, which should be connected by welding, already severely decreases the stability of the connection which is formed, if a connection is formed at all. Thus a mechanical contact is particularly advantageous before the welding is performed. Elastic deformability of one of the components is not a mandatory requirement for the welded connection, a mechanical abutment or a press fit can be sufficient already. However, the elastic deformation may increase the radial contact force and is thus advantageous.

As the welded connection 250 is located in the interior of the housing 100 and the area of the housing through which the radiation enters is not modified by the radiation as the housing is transparent, the welded connection cannot be visually identified from the exterior easily.

As is depicted, in the region, where the welded connection is formed, the housing 100 is circumferentially closed. That is to say, there may be no openings in the housing 100 which would be required for a resilient movement of a snap feature as in the case of the connection feature 230. Thus, a connection feature can be dispensed with. However, a connection feature may be provided in addition nevertheless. The housing 100 may be formed without lateral openings, except maybe for the window.

Principles of the present disclosure as discussed above are realized as well in the following embodiments, so that only the differences over the embodiments described above are discussed below.

Figure 4:
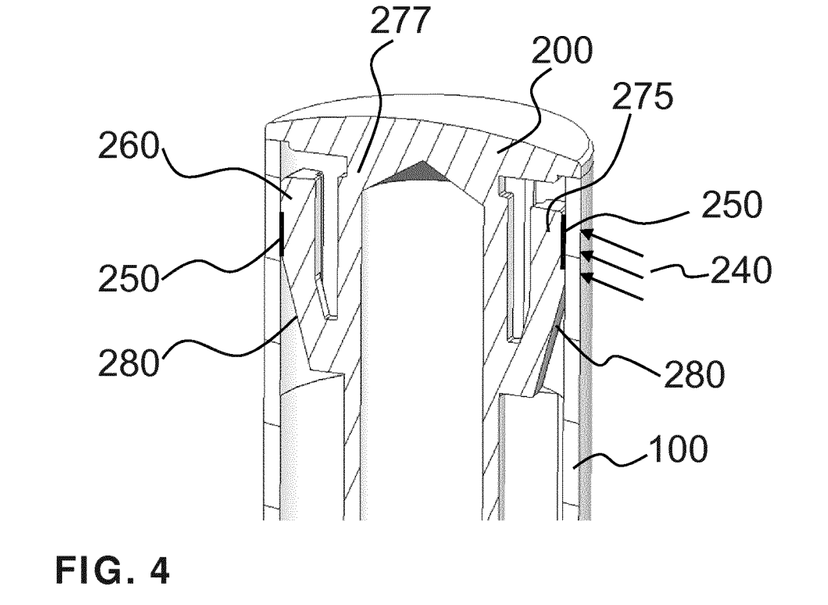

FIG. 4 illustrates a further embodiment on the basis of a schematic sectional view. Again, the closure part 200 is inserted into the housing 100 already. As opposed to the previous embodiment, the mechanical contact interface between the join partners—housing 100 and closure part 200—is formed by one resilient join feature which is resiliently connected to a body of the join partner. In the depicted embodiment, the closure part is provided with one or more join features 275, which are connected in a resiliently displaceable fashion to a main body 277 of the closure part 200. The join features 275 are preferably axially oriented. The join features 275 may be fingers or lugs, for example. When the closure part 200 is inserted into the housing 100, the join features 275 are elastically deformed, such as by being radially inwardly displaced. The according restoring force acts into the radial outward direction and, consequently, increases the contact force between the housing 100 and the join feature 275. While the closure part is inserted into the housing, a slanted or sloped surface 280 of the join feature, which may extend towards the main body 277 as seen from a free end of the join feature 275, may interact with the housing 100 to generate a radially inwardly directed force during the axial relative movement of the closure part 200 with respect to the housing 100. Different join features 275 are preferably oppositely disposed and/or uniformly distributed in the circumferential direction. A welded connection 250 may be employed at every join feature. A contact surface of the join feature with the inner surface may be axially oriented in the fitted configuration of the closure part 200, i.e. not slanted or sloped as the surface 280. This increases the contact area between the closure part 200 and the housing 100. As previously discussed, the housing 100 may be transparent, such that the laser radiation 240 can propagate through the wall of the housing and reach the closure part 200 and, specifically, the join feature 275 where the energy can be absorbed and the welded connection 250 can be generated as previously described.

Figure 5:
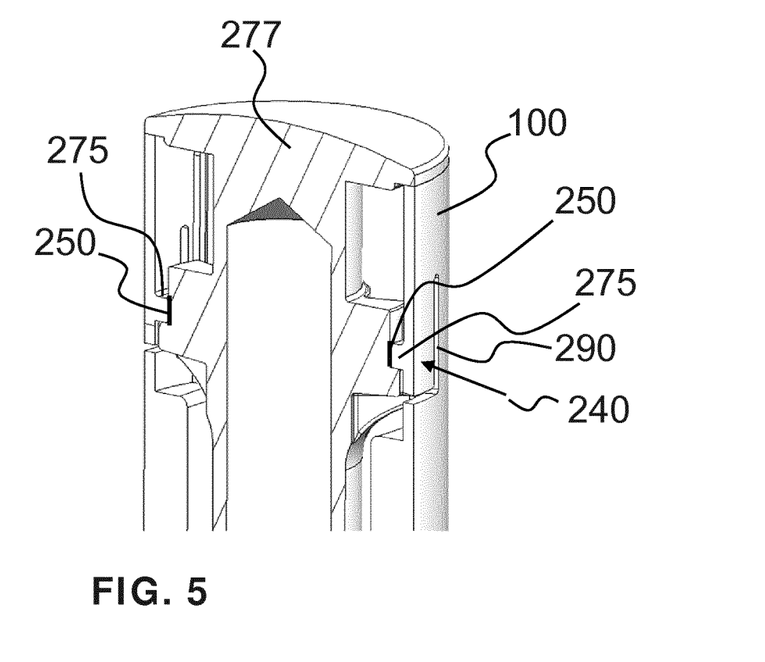

In FIG. 5, another exemplary embodiment is discussed on the basis of a schematic sectional view. In this embodiment, the (radially resilient) join feature 275 is not provided on the closure part 200 but rather on the housing 100. In the position depicted in FIG. 5, the radially inwardly directed force resulting from the radial outward displacement of the join feature 275 during the introduction of the closure part 200 into the housing 100 maintains the closure part surface and the join feature surface in mechanical contact. Thereafter, the contact area can be irradiated with the laser radiation 240 and the welded connection 250 can be formed as described previously.

As the join feature 275 has to be resiliently deflectable, a cut-out 290 is provided in the housing 100 around the join feature 260 in order to provide the respective flexibility. This cut-out, although the welded connection is preferably not visible from the outside, can be a region, where a user can tamper with the device. Accordingly, the solution provided in FIG. 4 may be advantageous, as the join feature 275 is not accessible from the exterior. However, the solution in FIG. 5 may nevertheless be employed as it is also tamper-evident, e.g. because the connection cannot be released without severely damaging the parts. If the solution of FIG. 5 is employed, it may be advantageous to cover the join feature 275 and/or the cut-out 290 with a label, for example. Alternatively, a resilient join feature 275 may be arranged at the interior of the housing where the outer surface is closed. This may, however, make moulding more difficult.

In the previously described embodiments, the housing 100 was transparent to the laser radiation. In the following embodiment, the housing 100 need not be transparent, but may be non-transparent for the laser radiation used to join the parts together. That is to say, if the housing were irradiated with the radiation, it would melt on the site of the exterior surface which is irradiated. However, the housing may, nevertheless, still be transparent in this embodiment.

Figure 6A:
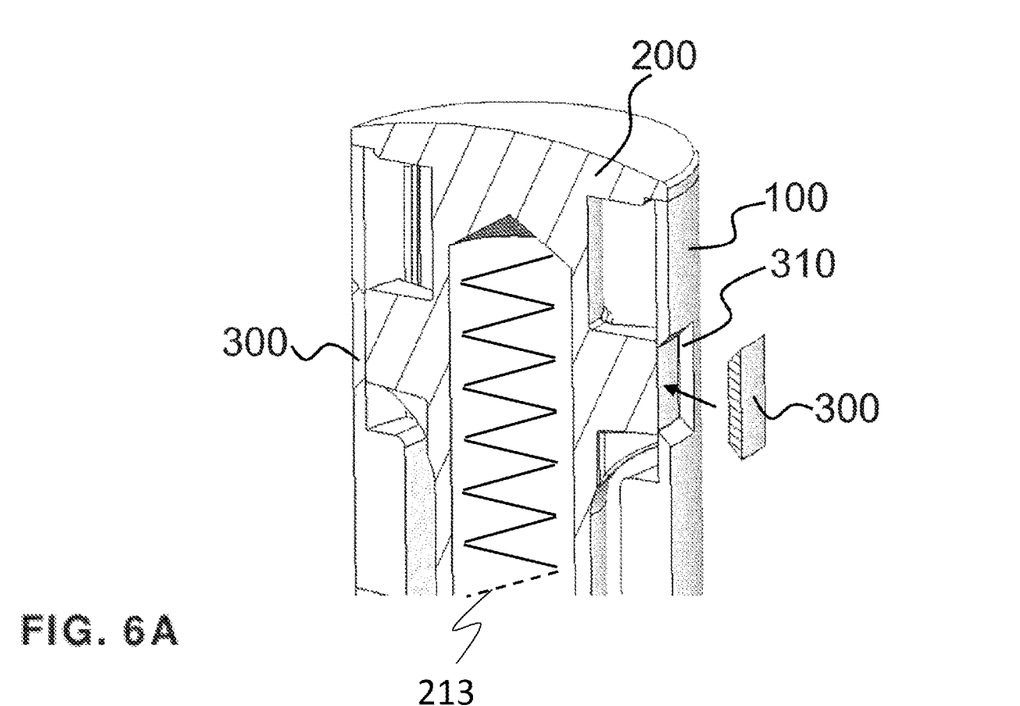
FIGS. 6A and 6B illustrate another embodiment of a drug delivery device having a welded connection and a method of manufacturing the device on the basis of schematic sectional views.
Figure 6B:
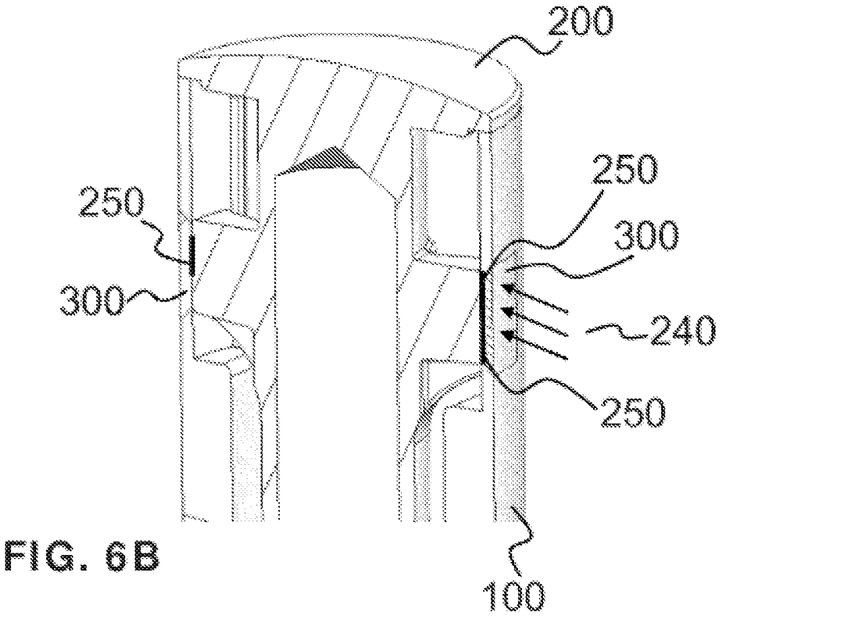

The according embodiment is illustrated in FIGS. 6A and 6B. FIG. 6A illustrates a situation before the welded connection is generated and FIG. 6B illustrates the situation during and/or after the welding is performed. Again, as in the previous embodiments, the closure part 200 has already been inserted into the housing 100. In this embodiment, however, the welded connection is not formed directly between the housing and the closure part. In this embodiment an additional part is employed for forming the connection with the closure part 200. This part is the securing part 300. As depicted in FIGS. 6A and 6B, the housing 100 comprises an aperture or opening 310. The opening is shaped to receive the securing part 300. FIG. 6A illustrates the situation before the securing part is inserted into the opening. In FIG. 6B, the part 310 has been inserted into the opening already. The opening 310 is provided in a side surface of the housing 100 which extends between or connects the proximal and the distal end of the housing 100. The opening 310 extends radially through the entire wall of the housing 100 form the exterior to the interior of the housing. The opening 310 is arranged and configured such that, if the closure part 200 has been introduced into the housing 100, that surface of the closure part 200, which shall establish the welded connection, is accessible through the opening. The surface may be axially aligned with the opening when the closure part 200 has been introduced into the housing 100 and has reached its intended end position in which it should be secured relative to the housing 100.

The securing part 300 is shaped such that it fits into the opening 310, e.g. wedge-like. The outer contour of the securing part 300 may match the inner contour of the opening 310. In particular, when arranged in the opening the securing part is preferably secured relative to the housing against axial—proximal and/or distal—movement and/or also angular movement, preferably in both rotational directions. The relevant axis for these movements may be the longitudinal axis of the housing. This restriction of the possibilities to move relative to the housing can be achieved by the matching inner and outer contours.

The securing part 300, the opening 310 and/or the closure part 200 are configured and/or adjusted to one another such that the securing part 300 abuts the closure part 200 when the securing part is arranged within the opening 310. Then, the welded connection may be formed by the laser radiation 240. Once the securing part 300 has been connected to the closure part 200 via the welded connection 250, the closure part 200 cannot be removed from the housing 100 without destroying the welded connection, as the securing part cannot be axially and/or angularly moved relative to the housing. Thus, if one wants to remove the closure part 200 the welded connection 250 has to be destroyed. If the connection is destroyed, the securing part falls out of the opening and cannot be easily reattached as its interior surface has already been melted once during the welding process.

The securing part 200 may have slanted side faces or straight side faces, i.e. oblique or parallel to an axis perpendicular to the longitudinal axis of the housing 100. The securing part 300 may be designed such that its outer surface is flush with the outer surface of the housing 100 or recessed inwardly once the closure part 200 and the securing part 300 have been connected to one another. The thickness of the securing part, e.g. its radial extension when it is arranged in the opening, may be greater than or equal to the depth of the opening, i.e. the radial extension of the opening. The thickness may be less than or equal to twice the depth of the opening. If the thickness of the securing part 300 is greater than the depth of the opening 310, the contact between the closure part and the securing part is inwardly offset from an inner surface of the housing, e.g. in the radial direction.

Thus, the area where the heat is generated may be offset inwardly from the housing. Consequently, the risk of damaging the housing 100 by transferring heat to it is reduced.

Figure 7:
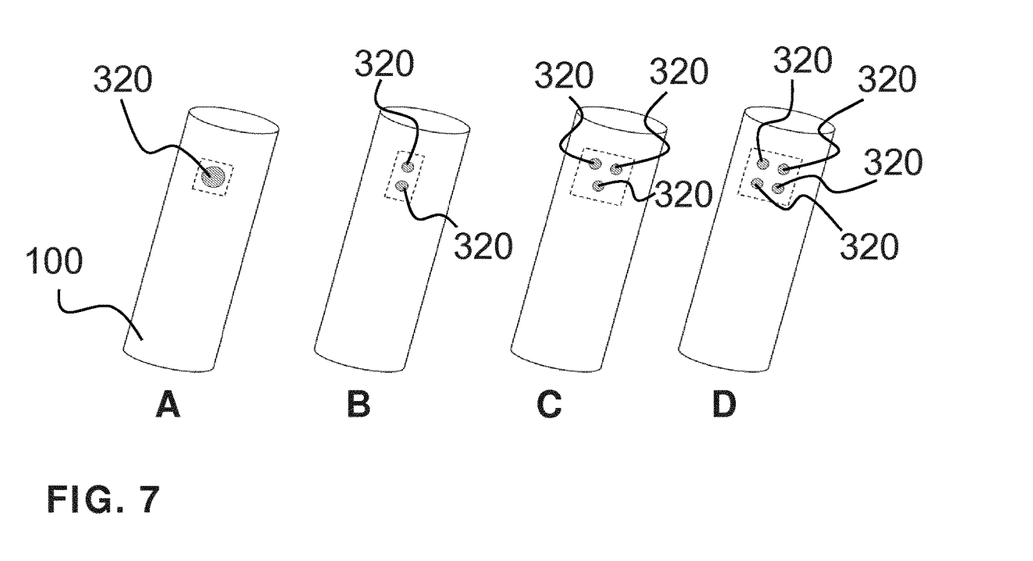
FIGS. 7A through 7D and 8A through 8D illustrate embodiments of a welded connection.

The welded connection can be realized in variety of ways, e.g. depending on how high the force is, which the welded connection has to or should be able to react. FIGS. 7 and 8 illustrate embodiments of a welded connection. The area where the welded connection 250 is formed, is delimited by the dashed line in the figures. For example, one, preferably large, weld or welded spot 320 can be employed for the welded connection as depicted in FIG. 7A or a plurality of welds 320 can be provided in one designated joining area, e.g. in one contact area between the closure part and the other join partner (housing or securing part). In FIG. 7B, two welds 320 of a welded connection are shown, which are angularly aligned and/or axially offset. Two of the welds 320 in FIG. 7C are axially aligned and angularly offset. Another weld 320 is angularly and axially offset from the axially aligned welds. In FIG. 7D four welds 320 are shown, which are pairwise axially and angularly aligned, e.g. arranged in a quadrangular pattern.

Figure 8:
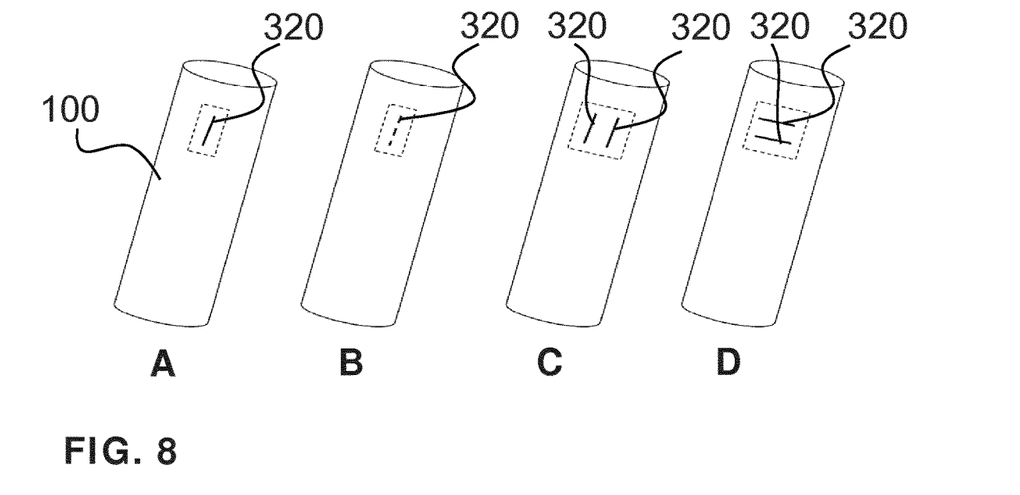

Other options of arranging the welds 320 or forming the welded connection 250 are shown in FIGS. 8A through 8D. Herein, the welds 320 are oriented along a line, i.e. the respective weld 320 has a distinguished direction of extension. In FIG. 8A, one axially oriented weld line, e.g. from the proximal to a distal end of the housing 100, is used. In FIG. 8B, the welded connection is realized by a plurality of linear welds 320, which are oriented along a common line in plan view which results in the appearance of a dashed line. In FIG. 8C, two line-like welds 320 are used, which are angularly offset, e.g. parallel in plan view, and/or axially aligned. In FIG. 8D, two axially off-set, e.g. parallel in plan view, and/or angularly aligned, line-like welds 320 are used.

What kind of shape and/or pattern of welds 320 is used for the welded connection may depend on the space or geometry, which is available in the device for forming the welded connection, the accessibility of the region of mechanical contact between the joining partners for the laser radiation, the forces, which have to be reacted or transferred via the welded connection, and/or the melting properties of the plastics involved. The appropriate pattern of welds may be selected to meet the needs of the respective system where the connection is employed.

As already discussed above, the presently proposed disclosure has the advantages, that manipulations in a drug delivery device, in particular an auto-injector, are made considerably more difficult, as components are mandatorily destroyed or severely damaged, when the device is disassembled. This damage can be easily perceived and/or prevent reassembling the device. Moreover, in most of the variants discussed above, no additional parts are used aside from the embodiment with the securing parting 310. Still further, the welded connection may not be visible to the user from the exterior.

It is even possible in the embodiment depicted in FIG. 2 to provide the connection feature 230 with a welded connection 250 to the closure part 200 in addition to its capability of connecting the housing and the closure part to one another, e.g. via a force-fit connection. The connection feature is used to establish a force-fit connection and a material connection with the housing. Accordingly, when it is attempted to tamper with the connection feature 230, the connection may be damaged. Thus, when it is attempted to disassemble the device the connection feature and/or its counterpart on the closure part 200 may be damaged such that the force-fit connection can no longer be established.

Figure 9:
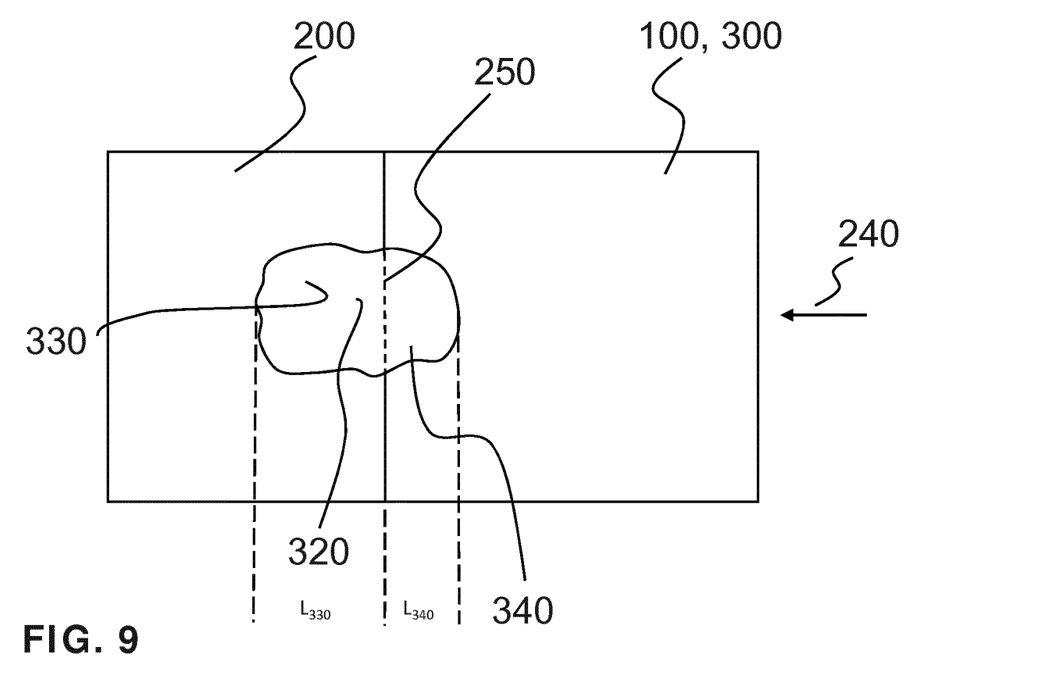
FIG. 9 illustrates a schematic view of a welded connection with molten and hardened areas.

FIG. 9 illustrates schematically the welded connection 250. FIG. 9 illustrates the region, where the two join partners, i.e. the closure part 200 and the housing 100 or the securing part 300, abut one another. The former border between the two components in the welded region is indicated by the dashed line. At the solid line outside of the connection 250, the join partners may still be in mechanical contact. As is apparent from the figure, within each of the parts (closure part 200 and housing 100 or securing part 300) a molten and hardened region 330, 340 is formed. These regions have different sizes as seen from the borderline between the two join partners. The region 340 which is arranged in that join partner, which is transparent for the laser radiation 240, has a smaller length or extension—in particular as seen along a direction away from the border between the two join partners and/or along the irradiation direction of the laser beam when irradiating the exterior surface—than the region 330 in the closure part 200. The associated extensions or lengths are highlighted in the figure by $L_{340}$ and $L_{330}$. The smaller length $L_{340}$ results from the transparency of the first join partner (housing 100 or securing part 300) as discussed previously already.

It should be readily apparent, that, instead of having the closure part 200, an additional part can be used just as was done with the securing part 300 in the housing. However, for a small part count, using the closure part 200 is advantageous. Although the embodiments involving the welded connections have been disclosed above in connection with specific parts as join partners, the disclosure extends to general join partners. That is to say, "housing", "closure part", "securing part" may be substituted by "join partner". Still further, instead of using laser welding, ultrasonic welding may be employed as well.

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

REFERENCE NUMERALS 100 housing
110 cap
120 window
130 reservoir
140 proximal opening
150 drug
160 bung
170 needle unit
180 needle cover
190 mechanism unit
200 closure part
210 bung driver
220 drug delivery device
230 connection feature
240 laser radiation
250 welded connection
260 surface
270 protrusion
275 join feature
277 main body
280 surface
290 cut out
300 securing part
310 opening 320 weld
330 area
340 area
L$_{330}$ length
L$_{340}$ length

The invention claimed is:

1. A drug delivery device comprising:
a housing defining an interior;
a reservoir that is adapted to contain a drug, the reservoir being retained in the interior; and
a closure part that is secured relative to the housing and that has to be disconnected from the housing to access the reservoir within the interior,
wherein the closure part is secured relative to the housing by a welded connection that is formed between a first join partner and a second join partner,
wherein the closure part is the second join partner,
wherein the first join partner is a securing part that is different from the housing,
wherein the housing comprises an aperture, and
wherein the first join partner is arranged in the aperture and is retained in the aperture by the welded connection to the second join partner.

2. The drug delivery device of claim 1, wherein each of the first and second join partners has at least one molten area and at least one hardened area that form the welded connection in a boundary region between the first and second join partners.

3. The drug delivery device of claim 1, wherein the welded connection is arranged closer to an exterior surface of the drug delivery device than to a surface of the second join partner that faces away from the welded connection.

4. The drug delivery device of claim 1, wherein the first join partner and the second join partner are configured to have different absorption coefficients for an electromagnetic radiation, and wherein a first absorption coefficient of the first join partner for the electromagnetic radiation is less than a second absorption coefficient of the second join partner for the electromagnetic radiation.

5. The drug delivery device of claim 4, wherein the second join partner comprises absorber particles configured to absorb the electromagnetic radiation.

6. The drug delivery device of claim 4, wherein the first join partner is transparent to the electromagnetic radiation.

7. The drug delivery device of claim 1, wherein at least one of the first and second join partners is elastically deformable, and/or wherein at least one of the first and second join partners comprises a join feature that is resiliently connected to a body of the at least one first or second join partner, and wherein the welded connection is formed between the join feature and the other of the at least one first or second join partner.

8. The drug delivery device of claim 1, wherein the housing comprises one of the first and second join partners.

9. The drug delivery device of claim 1, wherein the housing is tubular, and wherein the closure part closes a proximal end of the housing.

10. The drug delivery device of claim 1, further comprising a biased spring configured to drive dispensing of the drug from the reservoir, wherein the biased spring is reactable by the welded connection.

11. The drug delivery device of claim 1, wherein the drug delivery device comprises an auto-injector.

12. The drug delivery device of claim 1, further comprising the drug contained within the reservoir.

13. The drug delivery device of claim 1, wherein the housing is meltable by laser welding.

14. The drug delivery device of claim 13, wherein the housing is meltable by plastic-to-plastic laser welding.

15. The drug delivery device of claim 1, wherein the closure part is secured relative to the housing by a plastic-to-plastic laser welding connection.

16. The drug delivery device of claim 1, wherein the aperture is a first aperture, wherein the housing comprises a second aperture on its proximal end, and wherein the second aperture is configured to allow insertion of the closure part into the housing.

17. A method of manufacturing a drug delivery device, the method comprising:
providing a housing;
inserting a reservoir into the housing, the reservoir containing a drug;
arranging a closure part relative to the housing and the reservoir in a predetermined position;
securing the closure part relative to the housing by laser welding in the predetermined position, and
using a welded connection between two or more of the closure part, a first join partner, and a second join partner of the drug delivery device as an anti-counterfeiting feature or as a tamper indicator,
wherein each of the first and second join partners has at least one molten area and at least one hardened area that form the welded connection in a boundary region between the first and second join partners, and
wherein the welded connection is arranged closer to an exterior surface of the drug delivery device than to a surface of the second join partner that faces away from the welded connection.

18. The method of claim 17, wherein the first join partner and the second join partner are configured to have different absorption coefficients for an electromagnetic radiation, and wherein a first absorption coefficient of the first join partner for the electromagnetic radiation is less than a second absorption coefficient of the second join partner for the electromagnetic radiation.

19. The method of claim 18, wherein the second join partner comprises absorber particles configured to ab sorb the electromagnetic radiation, and/or wherein the first join partner is transparent to the electromagnetic radiation.

20. A method of manufacturing a drug delivery device, the method comprising:
providing a housing comprising a first aperture and a second aperture;
inserting a reservoir into the housing through the second aperture, the reservoir containing a drug;
arranging a closure part relative to the housing and the reservoir in a predetermined position through the second aperture;
arranging a securing part in the first aperture, and
securing the closure part relative to the housing in the predetermined position by laser welding of the closure part and of the securing part forming a connection.

* * * * *

UNITED STATES PATENT AND TRADEMARK OFFICE
CERTIFICATE OF CORRECTION

| | |
|---|---|
| PATENT NO. | : 12,042,643 B2 |
| APPLICATION NO. | : 17/252453 |
| DATED | : July 23, 2024 |
| INVENTOR(S) | : Ngoc Jane Lam and Tobias Stever |

It is certified that error appears in the above-identified patent and that said Letters Patent is hereby corrected as shown below:

In the Claims

Column 22, Line 45, Claim 19, delete "ab sorb" and insert -- absorb --

Signed and Sealed this
First Day of October, 2024

Katherine Kelly Vidal
*Director of the United States Patent and Trademark Office*